United States Patent [19]

Yoshioka et al.

[11] Patent Number: 5,512,159

[45] Date of Patent: Apr. 30, 1996

[54] BIOSENSOR

[75] Inventors: Toshihiko Yoshioka, Osaka; Mariko Kawaguri, Moriguchi; Shiro Nankai, Hirakata; Haruhiro Tsutsumi, Onsen; Hideyuki Baba, Matsuyama; Yoshinobu Tokuno, Matsuyama; Shoji Miyazaki, Matsuyama, all of Japan

[73] Assignee: Matsushita Electric Industrial Co. Ltd., Osaka, Japan

[21] Appl. No.: 293,131

[22] Filed: Aug. 19, 1994

Related U.S. Application Data

[63] Continuation of Ser. No. 881,634, May 12, 1992, abandoned.

[30] Foreign Application Priority Data

Jan. 21, 1992 [JP] Japan ..................... 4-008219

[51] Int. Cl.$^6$ ................................. G01N 27/327
[52] U.S. Cl. ..................... 204/403; 204/280; 204/412
[58] Field of Search ..................... 204/403, 412

[56] References Cited

U.S. PATENT DOCUMENTS 4,571,292  2/1986  Liu et al. ..................... 204/412
4,851,088  7/1989  Chandrasekhar et al. ............. 204/412
4,871,440  10/1989  Nagata et al. ..................... 204/412
4,897,173  1/1990  Nankai et al. ..................... 204/403
4,948,490  8/1990  Venkatasetty ..................... 204/412
5,120,420  6/1992  Nawkai et al. ..................... 204/403
5,126,034  6/1992  Carter et al. ..................... 204/412

FOREIGN PATENT DOCUMENTS

1-212345  8/1989  Japan .

*Primary Examiner*—T. Tung
*Attorney, Agent, or Firm*—Wenderoth, Lind & Ponack

[57] ABSTRACT

A biosensor of the present invention is provided with an insulating base plate, an electrode system mainly consisting of a working electrode and a counter electrode formed on the insulating base plate, and a reaction layer on the electrode system. The counter electrode is partially a circular arc. A manufacturing method of the biosensor of the present invention is comprised of a step to form a base by arranging leads, an electrode system, and an insulating layer on an insulating base plate, and a step to form a reaction layer mainly composed of an enzyme on the electrode system. Since the counter electrode is partially in the shape of a circular arc, the reaction layer is easily formed and prevented from delaminating, whereby the measuring accuracy, preservative properties and reliability of the biosensor are improved. The present invention enables highly efficient biosensors to be mass produced at low cost.

6 Claims, 8 Drawing Sheets

Fig.9 the concentration of glucose within the blood with use of the whole blood is necessitated.

BIOSENSOR

This application is a Continuation of now abandoned application Ser. No. 07/881,634, filed May 12, 1992.

BACKGROUND OF THE INVENTION

1. Field of the Invention

The present invention relates to a biosensor designed to quickly quantify with ease and high accuracy a specific component in various kinds of sample liquids, and a manufacturing method of the biosensor.

2. Description of the Prior Art

Various kinds of biosensors utilizing the specific catalytic effect of an enzyme have been developed in the past years, but a more accurate one is desired.

An example of the biosensor of the aforementioned type, namely, a glucose sensor applied in the clinical field will be depicted below.

Conventionally, blood plasma obtained from the blood of a patient has been centrifugated and measured in order to quantify glucose included in the blood. This method requires time and labor. Therefore, such a sensor that can measure the concentration of glucose within the blood with use of the whole blood is necessitated.

As a simple glucose sensor, one similar to a test paper used for inspection of urea has been provided. This glucose sensor has a stick-like supporting body and a carrier fixed to the supporting body which includes an enzyme reacting only to glucose and a coloring matter changed by the substance resulting from the enzyme reaction. When the blood is dropped onto the carrier of the sensor and the change of the coloring matter after a predetermined time is measured by the naked eye or by an optical means, the amount of glucose in the blood can be known. According to the quantifying method using the glucose sensor of this type, however, the result is greatly influenced by the coloring matter in the blood, and therefore the measuring accuracy of the method is low.

According to a different method, a specific component of a living sample such as blood or the like can be quantified with high accuracy without requiring dilution or stirring of the sample liquid. An example of a biosensor executing the above method is proposed in Japanese Patent Laid-open Publication Tokkaihei 1-212345 (212345/1989), which will be discussed below.

The biosensor has an electrode system formed on an insulating base plate by screen printing or the like method, and an enzyme reaction layer which consists of a hydrophilic polymer layer, a oxidoreductase and an electron acceptor is formed on the electrode system.

The biosensor of the above structure operates in a manner as follows. When a sample liquid is dropped on the enzyme reaction layer, the oxidoreductase and electron acceptor are dissolved in the sample liquid, so that the enzyme reaction progresses with a substrate in the sample liquid. As a result, the electron acceptor is reduced. After the enzyme reaction is completed, the reduced electron acceptor is electrochemically oxidized. The concentration of the substrate in the sample liquid is obtained from an oxidization current obtained at this time.

In the conventional biosensor, the working electrode and counter electrode are formed of a material different from that of the insulating layer. Therefore, the reaction layer on the electrode system mainly consisting of the working electrode and counter electrode is formed in conformity with the configuration of the counter electrode. Since the counter electrode of the conventional biosensor is polygonal and mainly square, the reaction layer is apt to be separated from a corner of the counter electrode.

SUMMARY OF THE INVENTION

The object of the present invention is therefore to provide an improved biosensor comprised of an insulating base plate having an electrode system consisting of at least a working electrode and a counter electrode, and a reaction layer provided on the electrode system, wherein the counter electrode is provided with a circular arc portion at the outer edge of the counter electrode against the direction of sample supply containing the substrate to be measured. More preferably, the counter electrode is provided with an outer edge which is partially broken.

A biosensor according to a further aspect of the present invention is characterized in that the working electrode is provided with an outer edge which is circular, elliptical, deformed from the circular shape, or mainly polygonal the vertex of which assumes a curve.

A biosensor according to still another aspect of the present invention is characterized in that the distance between the counter electrode and working electrode is held equal.

The present invention further features a manufacturing method of the biosensor, which is comprised of a manufacturing step of a base whereby leads, an electrode system mainly constituted of a working electrode and a counter electrode and, an insulating layer are formed on an insulating base plate, and a forming step whereby a reaction layer mainly composed of an enzyme is formed onto the working electrode. The manufacturing step of the base includes the following three processes: a process to form the leads on the insulating base plate; a process to form the electrode system mainly constituted of the working electrode and counter electrode onto the insulating base plate; and a process to form the insulating layer on the insulating base plate.

The disadvantages inherent in the prior art can be solved by the biosensor of the present invention.

Moreover, the following effects can be achieved by the aforementioned means. In the first place, since the counter electrode is circular, elliptical or deformed from the circular shape, formation of the reaction layer becomes easy and delamination thereof can be prevented.

Further, since the working electrode is formed circular, elliptical, deformed from the circular shape, or mainly polygonal with a vertex thereof turned round by a curve, the density distribution of a current between the working and counter electrodes is made uniform. This is further enhanced by keeping the distance of the counter electrode from the working electrode equal. Consequently, the concentration of the substrate can be measured with higher accuracy.

Likewise, if a part of the circular or deformed counter electrode is removed, the lead part of the working electrode iv prevented from being shortcircuited with the counter electrode at the presence of a pin hole in the insulating layer, etc.

According to the manufacturing method of the present invention, in the case where the electrode system is made of the working and counter electrodes, that is, the electrode system is a system of two electrodes, the working and counter electrodes can be manufactured in one process although they have been conventionally formed in different processes, thereby reducing the number of manufacturing processes of the biosensor.

BRIEF DESCRIPTION OF THE DRAWINGS

These and other objects and features of the present invention will become clear from the following description taken in conjunction with the preferred embodiments thereof with reference to the accompanying drawings throughout which like parts are designated by like reference numerals, and in which.

BEST MODE FOR EXECUTING THE PRESENT INVENTION (Embodiment 1)

A glucose sensor will be described hereinbelow as one example of a biosensor of the present invention.

Figure 1:
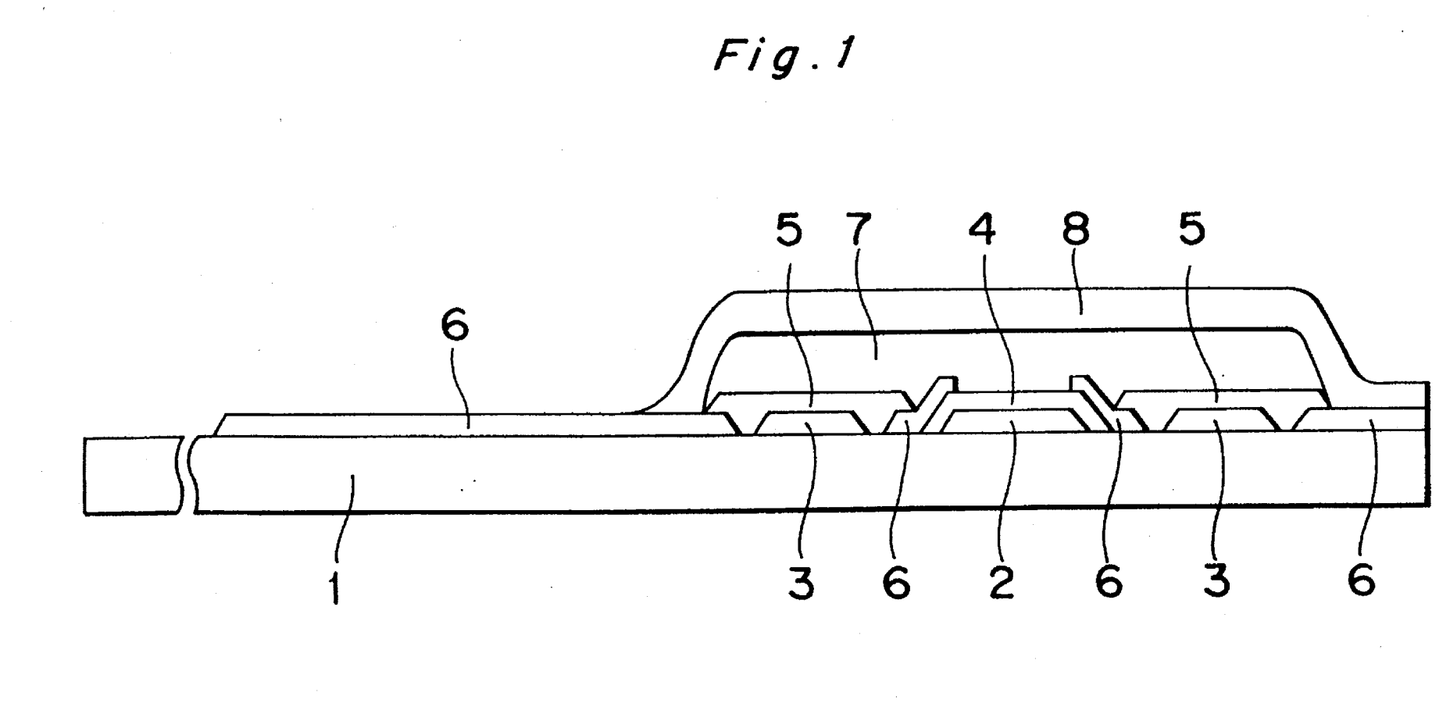
FIG. 1 is a cross sectional view of a glucose sensor without a cover and a spacer according to one embodiment of the present invention.
Figure 2:
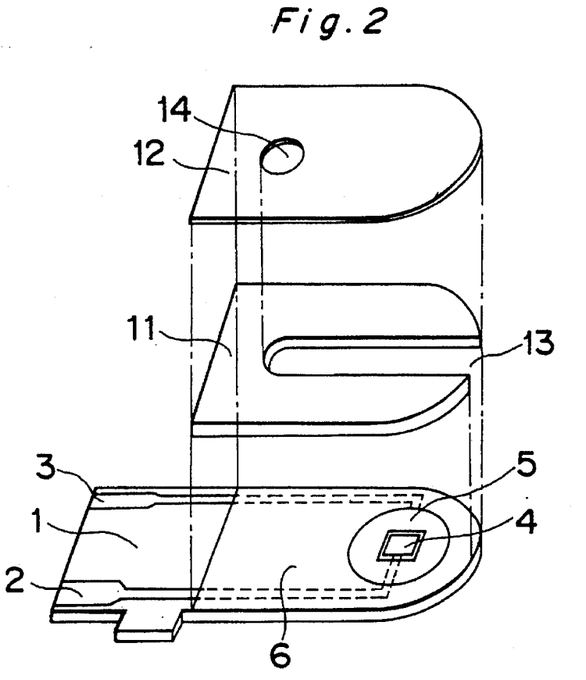
FIG. 2 is an exploded perspective view with a reaction layer removed from the glucose sensor of FIG. 1.

FIG. 1 is a cross sectional view of a glucose sensor without a cover and a spacer according to one embodiment of the present invention, and FIG. 2 is an exploded perspective view with a reaction layer removed from the glucose sensor.

Referring to these drawings, silver paste is printed on an insulating base plate 1 of polyethylene terephthalate through screen printing, thereby forming leads 2, 3. Conductive carbon paste including a resin binder is further printed in contact with the lead 2, thereby forming a working electrode 4. Then, insulating paste is printed to form an insulating layer 6.

The insulating layer 6 covers the outer periphery of the working electrode 4, so that the area of the exposed part of the working electrode 4 is held constant. At the same time, the insulating layer 6 covers the unnecessary part of the leads 2, 3. More specifically, the unnecessary part of the lead 2 is that portion which does not connect lead 2 with a working device. The unnecessary part of the lead 3 is that portion which does not connect the lead 3 with a counter electrode 5 which will be described later and which does not connect with the measuring device. The glucose sensor is connected to the measuring device via end parts of the leads 2, 3. The measuring device impresses a constant voltage to an electrode system which will be described later, and reads the value of the oxidation current.

The counter electrode 5 is formed by printing conductive carbon paste including a resin binder into contact with the lead 3, which is circular in the outer periphery thereof.

0.5 wt % solution of carboxymethyl cellulose (referred to as CMC hereinafter) as hydrophilic polymer in water is spread onto the electrode system consisting of the working electrode 4 and counter electrode 5 and dried, so that a CMC layer is formed.

The surface of the insulating layer according to the instant embodiment is water-repellent, and therefore the CMC aqueous solution is repelled by the insulating layer and spreads only over the electrode system of the working and counter electrodes 4, 5. If the counter electrode 5 is circular as illustrated in FIG. 2, it is possible to form the CMC layer uniform. Moreover, delamination of the layer which sometimes occurs after drying when the counter electrode is square can be prevented.

Subsequently, a mixed solution obtained by dissolving glucose oxidase (referred to as GOD hereinafter) as an enzyme and potassium ferricyanide as an electron acceptor in 0.5 wt % CMC aqueous solution is dropped onto the CMC layer, dried for ten minutes in a warm drier at 50° C. As a result, a reaction layer 7 is formed.

A solution of lecithin in toluene as a surface-tension surfactant is spread from a part of the base plate 1 corresponding to a sample feed port 13 onto the reaction layer 7 and dried, and a lecithin layer 8 is formed.

The insulating base plate 1, a spacer 11 and a cover 12 are bonded to each other in the positional relation as indicated by a chain line in FIG. 2.

3 μl glucose standard solution is supplied as a sample liquid from the sample feed port 13 to the glucose sensor formed in the above-described manner.

When the sample liquid is brought in touch with the sample feed port 13, it is also in touch with the lecithin layer 8 and smoothly guided onto the reaction layer by the lecithin layer.

It is not always necessary to distinguish the sample feed port 13 from an air hole 14. The sample liquid may be supplied from the air hole 14 as the sample feed port 13 functions as an air hole. In this case, if the air hole 14 is formed so that at least a part of the reaction layer comes immediately below the air hole 14, the lecithin layer 8 is possible to be abbreviated.

One minute after the sample liquid is fed to the glucose sensor, +0.5 V pulse voltage is impressed between the working electrode and the counter electrode. An oxidization current five seconds later is measured.

When the sample liquid is supplied to the glucose sensor, the reaction layer 7 is dissolved into the sample liquid, and glucose in the sample liquid is oxidized by the GOD. At this time, potassium ferricyanide is reduced to potassium ferrocyanide by the transferred electrons, and the oxidization current based on the concentration of the generated potassium ferrocyanide is allowed to flow because of the impression of the pulse voltage. The current is proportional to the concentration of the substrate, namely, glucose.

When the response characteristic of the glucose sensor of the instant embodiment is measured, favorable linearity is confirmed down to a concentration not smaller than 900 mg/dl (0.05 mol/l). Moreover, a coefficient of variation (CV value) is as good as approximately 2% when 50 glucose sensors are used.

(Embodiment 2)

Figure 3:
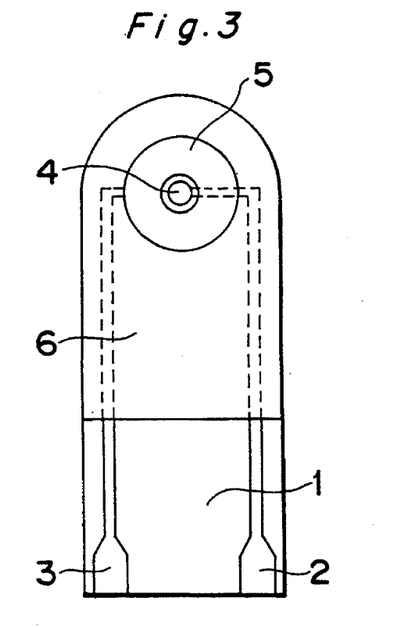
FIG. 3 is a plan view of a base of a glucose sensor according to a further embodiment of the present invention.

FIG. 3 is a plan view of a base when the counter and working electrodes are circular.

On an insulating base plate 1 formed of polyethylene terephthalate, there are formed leads 2, 3, a working electrode 4, an insulating layer 6 and a counter electrode 5 in the same manner as in Embodiment 1 above through screen printing. The base shown in FIG. 3 is thus obtained.

0.5 wt % CMC aqueous solution is spread and dried on an electrode system of the working and counter electrodes 4, 5, constituting a CMC layer. After being dissolved in a phosphate buffer solution (PH=5.6) GOD is dropped onto the CMC layer and dried to form a CMC-GOD layer. Moreover, a solution of 0.5 wt % polyvinyl pyrrolidone (referred to as PVP hereinafter) in ethanol as hydrophilic polymer is spread and dried to form a PVP layer. Potassium ferrioyanide of minute crystals is mixed in solution of 0.5% lecithin in toluene as a dispersant, which is dropped and dried on the PVP layer thereby to form a potassium ferricyanide-lecithin layer. In this manner, a reaction layer is formed.

Then, toluene solution in lecithin is spread as a surfactant from a part on the base plate corresponding to a sample feed port onto the reaction layer and dried, thus constituting a lecithin layer.

The insulating base plate is formed into one body with a spacer and a cover in the same manner as in Embodiment 1. Accordingly, a biosensor according to the second embodiment is obtained.

Similar to Embodiment 1, if an air hole is formed at such a position that at least a part of the reaction layer comes immediately below the air hole, the lecithin layer may be abbreviated. It is preferable in this case to supply the sample liquid from the air hole, as in Embodiment 1.

3 µl whole blood of a man is supplied as a sample liquid to the glucose sensor of the above-described structure. One minute later, +0.5 V pulse voltage is applied between the working electrode and the counter electrode. When an oxidization current five minutes later is obtained, good linearity is observed down to a concentration of glucose in the whole blood not lower than 450 mg/dl (0.025 mol/l). Moreover, when 30 sensors are used for the same sample of the whole blood, 2% or lower coefficient of variation (CV value) is measured.

A comparative glucose sensor having a square working electrode with the same area as in FIG. 2 is manufactured in the same fashion. However, the coefficient of variation to the whole blood is about 4% when 30 sensors are used. Therefore, if the working electrode is made circular without a vertex, higher accuracy is achieved in measurement.

(Embodiment 3)

Figure 4:
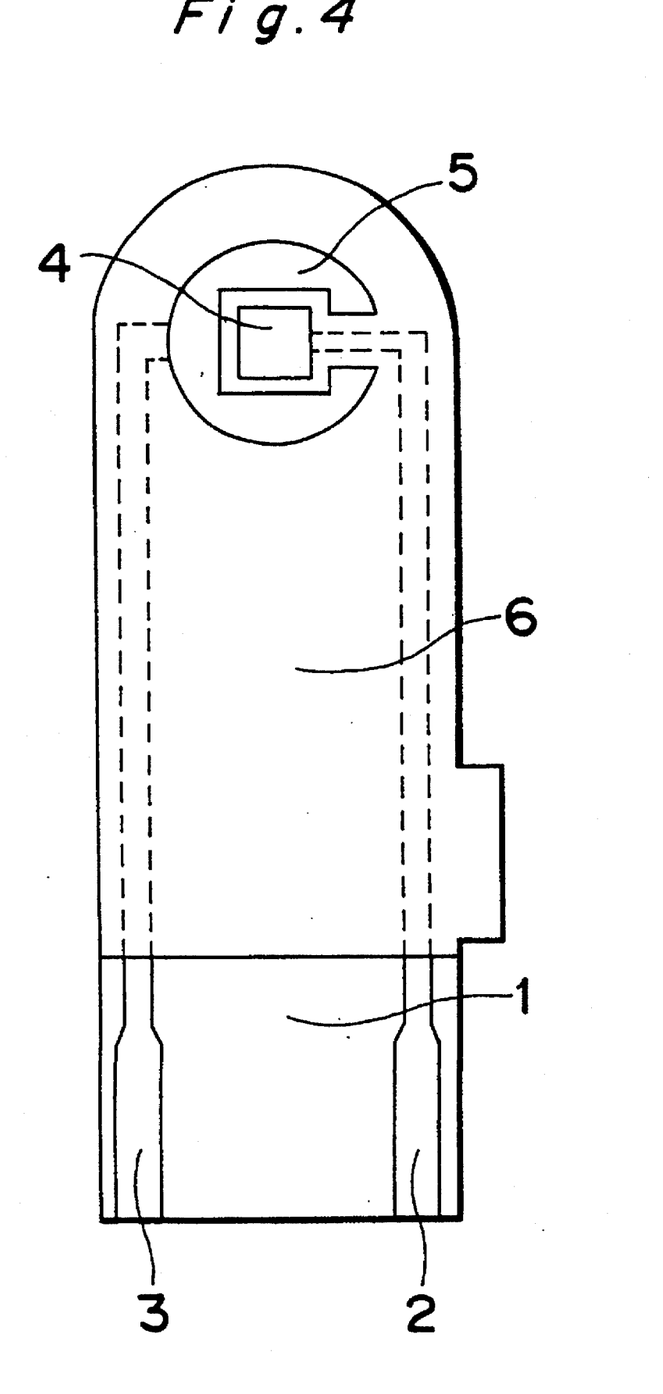
FIG. 4 is a plan view of a base of a glucose sensor according to a still further embodiment of the present invention.
Figure 5:
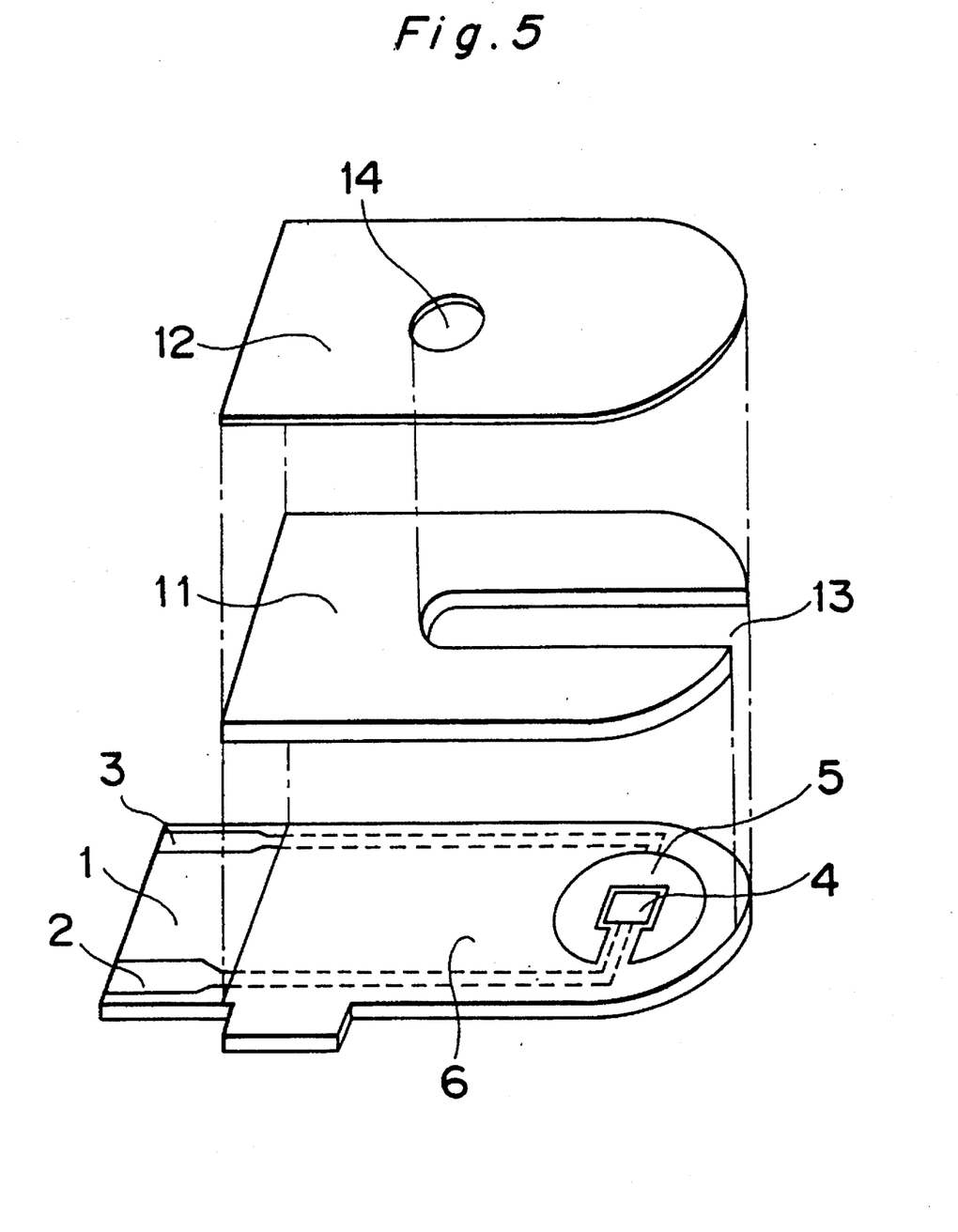
FIG. 5 is an exploded perspective view with a reaction layer removed from the glucose sensor of FIG. 4.

FIG. 4 is a plan view of a base of a glucose sensor according to a third embodiment of the present invention, and FIG. 5 is an exploded perspective view wherein a reaction layer is removed from the glucose sensor of FIG. 4.

Silver paste is printed by screen printing on an insulating base plate 1 of polyethylene terephthalate, so that leads 2, 3 are formed.

Then, conductive carbon paste including a resin binder is printed to form a working electrode 4 and a counter electrode 5. The working and counter electrodes 4, 5 are kept in touch with the leads 2, 3, respectively.

Insulating paste is then printed to form an insulating layer 6.

The insulating layer 6 covers the outer periphery of the working and counter electrodes 4, 5. The area of the exposed part of the working electrode 4 is maintained constant.

Moreover, the unnecessary part of the leads 2, 3, that is, that portion which does not connect with a measuring device, is covered with the insulating layer 6. The glucose sensor is connected to the measuring device by the end parts of the leads 2, 3. The measuring device functions to impress a constant voltage to an electrode system which will be described later and to read an oxidization current, etc.

According to the third embodiment, the working electrode 4 and counter electrode 5 are manufactured in one printing process, so that the number of manufacturing processes of the glucose sensor is reduced.

The counter electrode 5 is mainly circular, but a part thereof is notched as shown in FIG. 4. The insulating layer 6 is present in the cut part, and the lead 2 in touch with the working electrode 4 is provided below the insulating layer 6. Accordingly, even if a pin hole is found at a part of the insulating layer 6 corresponding to the cut part, the counter electrode 5 is prevented from being shortcircuited with the lead 2.

According to the manufacturing method described above, a large quantity of disposable glucose sensors can be manufactured at low cost with good yield.

0.25 wt % CMC aqueous solution is spread and dried on the electrode system comprised of the working and counter electrodes 4, 5, so that a CMC layer is formed.

As mentioned before, the insulating layer 6 is present at the cut part of the counter electrode 5. The surface of the insulating layer is water-repellent in the instant embodiment. Therefore, if the area of the cut part is large, the CMC aqueous solution is repelled by the insulating layer, thereby making it impossible to form the CMC layer uniform on the electrode system. For the above reason, it is desirable to set the distance or length of the cut part of the electrode 5 to be not larger than 2 mm, preferably not larger than 1.6 mm.

A mixed solution obtained by dissolving GOD and potassium ferricyanide in 0.25 wt % CMC aqueous solution is dropped onto the CMC layer, and dried for ten minutes within a warm drier at 50° C. A reaction layer is formed.

Toluene solution in lecithin as a surfactant is spread and dried onto the reaction layer from a part of the base plate 1 corresponding to a sample feed port 13, thereby forming a lecithin layer.

The insulating base plate 1 is bonded to a spacer 11 and a cover 12 as indicated by a chain line in FIG. 5.

When the sample liquid is brought in touch with the sample feed port 13, the sample liquid comes in contact with the lecithin layer as well. Accordingly, the sample liquid can be smoothly introduced onto the reaction layer by the lecithin layer.

As in Embodiment 1, the sample feed port 13 is not necessarily distinguished from an air hole 14.

Moreover, if the air hole is formed so that at least a part of the reaction layer is immediately below the air hole, the lecithin layer may be abbreviated. In such case as above, similar to Embodiment 1, the sample liquid is preferable to be supplied from the air hole.

When the concentration of glucose in a glucose standard solution is measured with use of the glucose sensor manufactured in the above-described manner, a response characteristic with good reproducibility is obtained.

(Embodiment 4)

On a base plate 1 which is insulating and formed of polyethylene terephthalate, leads 2, 3 are formed by printing silver paste through screen printing.

Insulating paste is further printed to form an insulating layer 6.

The insulating layer 6 covers the unnecessary parts of the leads 2, 3. The unnecessary part of the lead 2 is that portion which does not connect with a working electrode 4 to be described later and with a measuring device. On the other hand, the unnecessary part of the lead 3 is that portion which does not connect with a counter electrode 5 which will be discussed later and with the measuring device.

Thereafter, conductive carbon paste including a resin binder is printed, thereby forming the working electrode 4 and counter electrode 5. The working electrode 4 is in touch with the lead 2, while the counter electrode 5 is held in touch with the lead 3. In the manner as above, a base of FIG. 4 is manufactured.

According to this Embodiment 4, both the working electrode 4 and counter electrode 5 are formed in one printing process, so that the number of manufacturing processes of the base can be reduced.

Furthermore, according to Embodiment 4, since the distance between the electrodes 4 and 5 is determined by a screen formplate used in the third step of the manufacturing process of the base, the relative position of the electrodes 4, 5 is not changed even if the printing position is shifted when the insulating layer is formed in the second step.

Accordingly, it becomes possible to manufacture a mass of disposable glucose sensors at low costs with good yield.

Then, a reaction layer and a lecithin layer are formed in the same manner as in Embodiment 3, and the obtained base plate is integrally formed with a cover and a spacer. A glucose sensor of the fourth embodiment is thus provided.

When the concentration of glucose is measured in the same manner as. in Embodiment 3, a response with good reproducibility is obtained.

(Embodiment 5)

Figure 6:
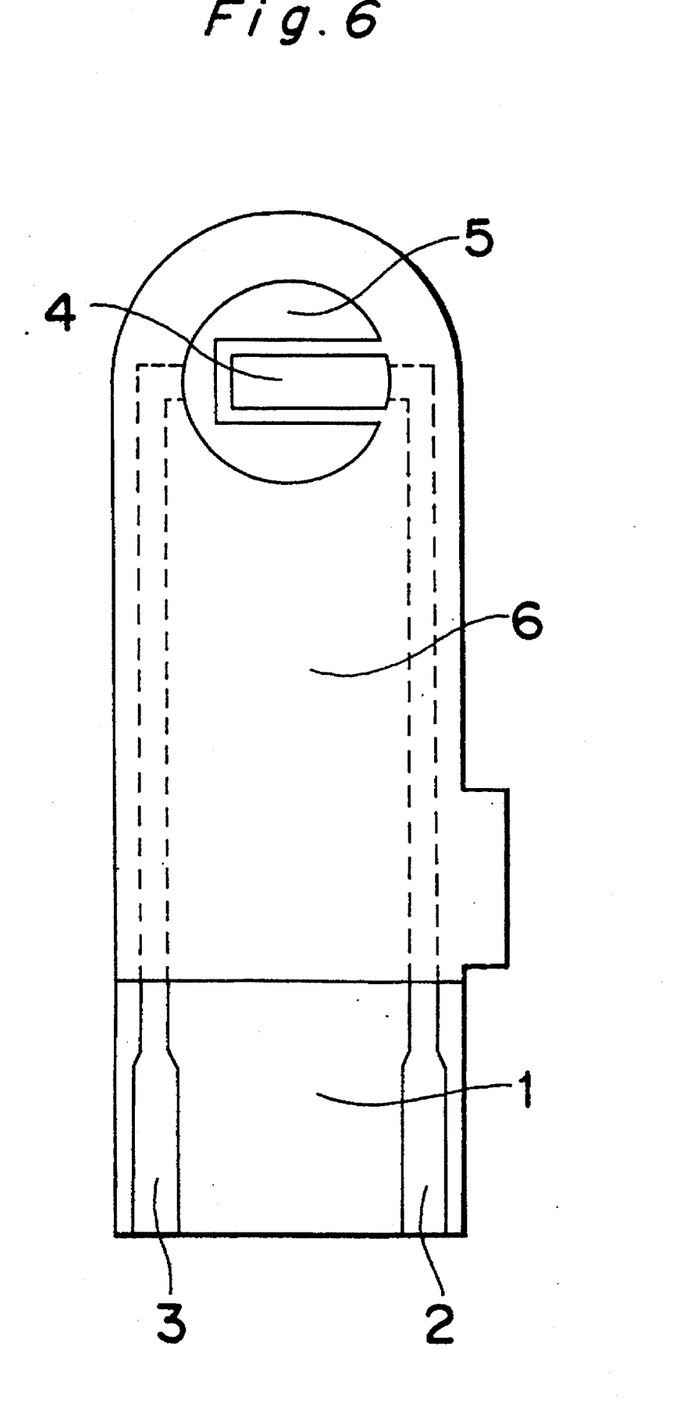
FIGS. 6, 7, 8, and 9 are plan views of a base of a glucose sensor according to still different embodiments of the present invention.

A base shown in FIG. 6 is formed through screen printing in the same fashion as in Embodiment 3.

When a working electrode 4 and a counter electrode are in the shape as in FIG. 6, the following effects are realized:

The number of manufacturing processes can be reduced as the electrodes 4, 5 are printed simultaneously;

A uniform reaction layer can be formed on an electrode system of the working and counter electrodes 4, 5 if the electrodes 4, 5 are made of the same material; and A lead 2 which is connected to the working electrode 4 is prevented from being shortcircuited with the counter electrode 5.

The glucose sensor of Embodiment 5 is formed in the same manner in the succeeding steps as in the third embodiment, which shows a response characteristic with good reproducibility in measuring the concentration of glucose.

(Embodiment 6)

Figure 7:
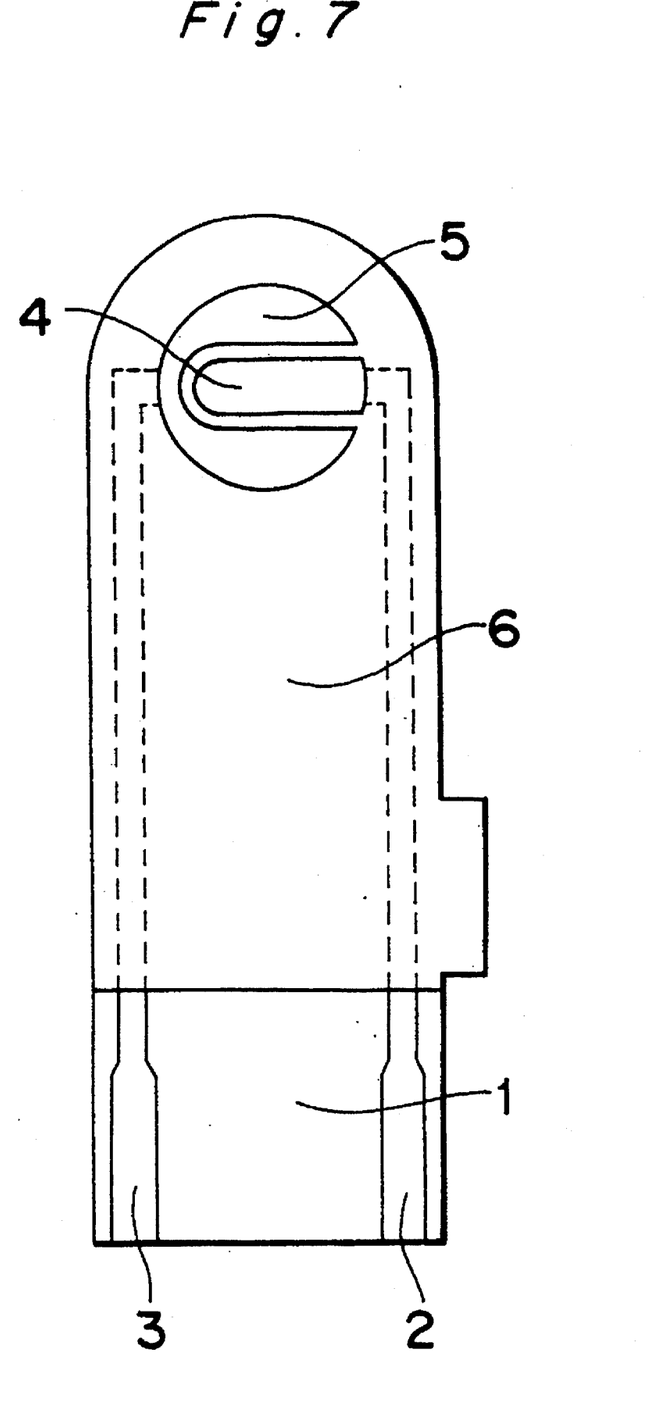

A base in FIG. 7 is obtained in the same manner as in Embodiment 3 through screen printing.

Since a working electrode 4 and a counter electrode 5 are formed in the shape as indicated in FIG. 7, such effects as follow are achieved:

The number of manufacturing processes can be reduced as the working electrode 4 and counter electrode 5 are printed at the same time;

A uniform reaction layer is formed on an electrode system comprised of the working and counter electrodes 4, 5;

Shortcircuiting between the lead 2 connected to the working electrode 4 and counter electrode 5 can be prevented;

Since the distance between the working electrode 4 and counter electrode 5 is held constant, and no vertex is present in the working electrode 4, highly accurate measurement is realized.

Subsequently, the glucose sensor of Embodiment 6 is formed in the same manner as in Embodiment 3. When the concentration of glucose is measured by the glucose sensor, the glucose sensor shows a response characteristic with good reproducibility.

(Embodiment 7)

Figure 8:
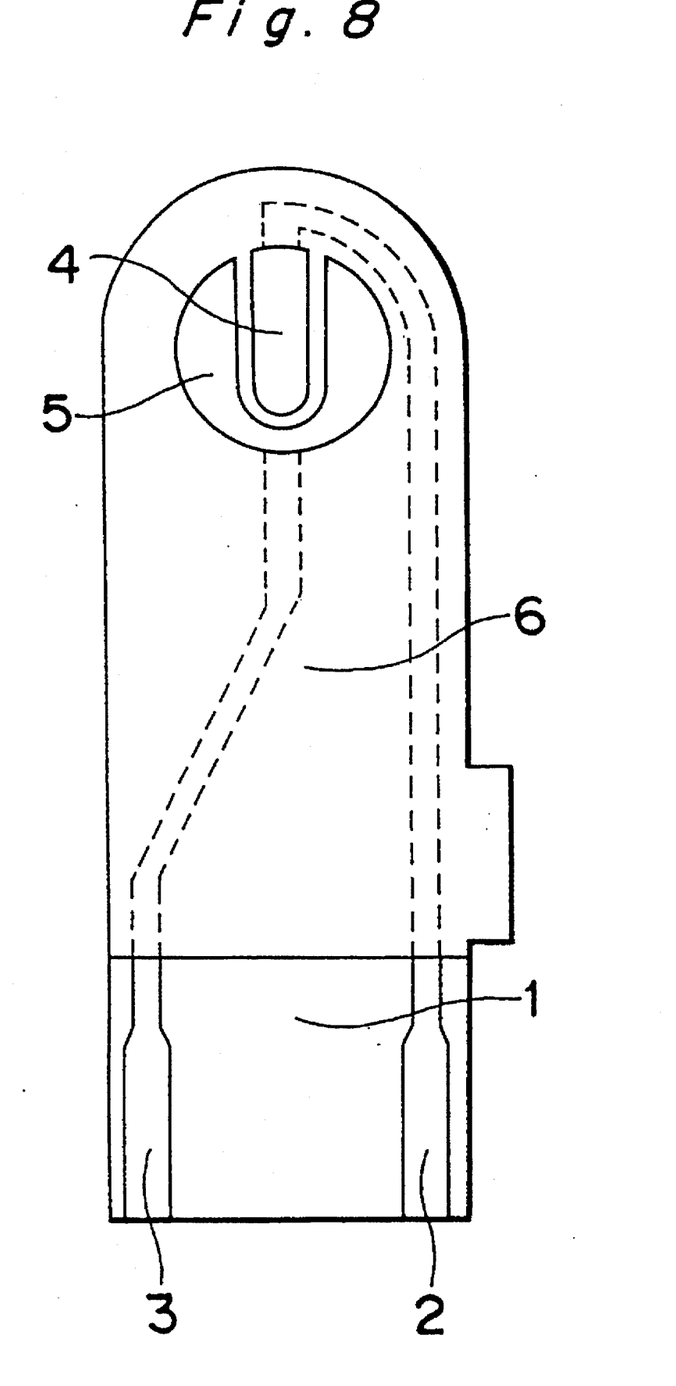

A base is formed as indicated in FIG. 8 through screen printing in the same manner as in Embodiment 4.

Since a working electrode 4 and a counter electrode 5 are formed in the shape as shown in FIG. 8, a glucose sensor of Embodiment 7 enjoys the following effects:

The number of manufacturing processes can be reduced by printing the working electrode 4 and counter electrode 5 simultaneously;

A uniform reaction layer can be formed on an electrode system comprised of the working and counter electrodes 4 and 5 if the electrodes 4, 5 are made of the same material;

A lead connected to the working electrode 4 can be prevented from being shortcircuited with the counter electrode The distance from the working electrode 4 to the counter electrode 5 is kept constant, and the working electrode 4 has no vertex, whereby the concentration can be measured with higher accuracy.

In addition to the above, a further effect can be obtained:

Since the working and counter electrodes 4, 5 are formed on an insulating layer 6, a step difference is generated at a part of the insulating layer held between the electrodes 5 and 4. A sample liquid is fed from a sample feed port, and does not intersect the step difference until the liquid reaches the working electrode. As a result, the reaction layer can be uniformly dissolved into the sample liquid, thereby improving the measuring accuracy.

The glucose sensor is manufactured subsequently in the same manner as in Embodiment 4, which shows a response characteristic with good reproducibility when measuring the concentration of glucose.

Figure 9:
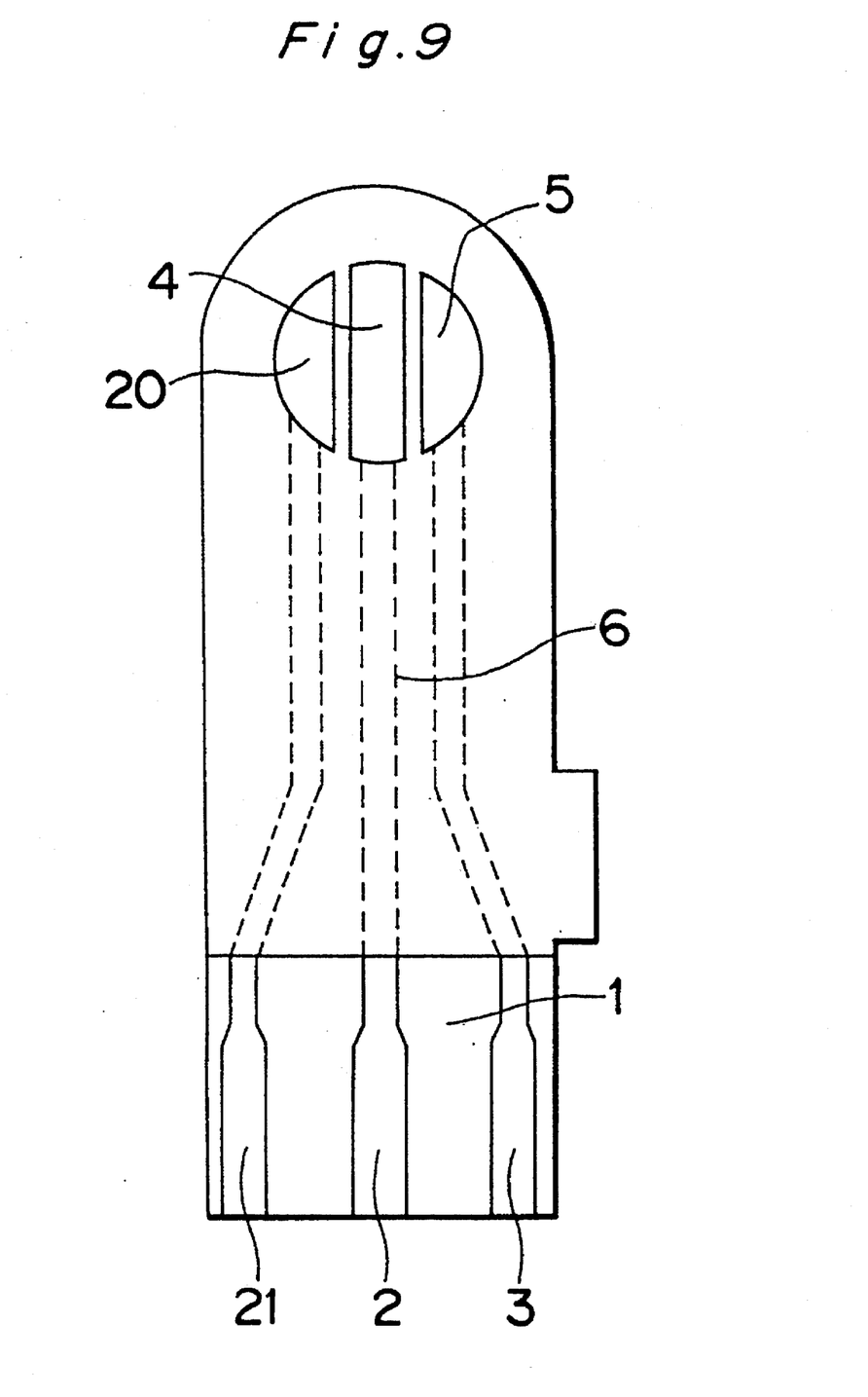

If the electrode system of two electrodes, namely, working electrode 4 and counter electrode 5, is turned to an electrode system of three electrodes wherein a reference electrode 20 and a lead 21 are added as shown in FIG. 9, the concentration can be measured more correctly.

In the foregoing embodiments, even when the working electrode or counter electrode is changed from circular to elliptical, the identical effects are achieved. The electrode may not be always a true circle or a true ellipse, and can be deformed from a circle or an ellipse so long as the above effects are ensured.

Although the foregoing embodiments are all related to a glucose sensor, the present invention is widely applicable to an enzyme-related system such as a sucrose sensor, a fructose sensor, an alcohol sensor, a lactic acid sensor, a cholesterol sensor, an amino acid sensor, etc.

Further, in place of glucose oxidase used as an enzyme in the above embodiments, invertase, mutarotase, fructose dehydrogenase, alcohol oxidase, lactate oxidase, lactate dehydrogenase, cholesterol oxidase, amino acid oxidase, xanthine oxidase or the like may be employed.

Carboxymethyl cellulose and polyvinyl pyrrolidone are used as hydrophilic polymer in the above embodiments. However, it is not restricted to these, but polyvinyl alcohol, gelatine and its derivative, acrylic acid and its salt, methacrylic acid and its salt, starch and its derivative, maleic anhydride and its salt, and cellulose derivative may be used. More specifically, there are, for cellulose derivatives, hydroxypropyl cellulose, hydroxyethyl cellulose, methyl cellulose, ethyl cellulose, ethyl hydroxyethyl cellulose, carboxymethyl ethyl cellulose.

According to Embodiment 2, lecithin is used as a dispersant. However, the dispersant is not particularly restricted to lecithin so long as it does not influence the activity of the enzyme. For instance, polyoxyethylene alkyl ether, polyethylene glycol fatty ester, oleic acid, polyoxyethylene glycerin fatty acid, cyclodextrin, etc. may be employed.

Moreover, as an electron acceptor, p-benzoquinone, phenazine methosulfate, ferrocene and the like can be used besides potassium ferricyanide in the foregoing embodiments.

As is clearly described hereinabove, the biosensor of the present invention is capable of measuring a specific component in various kinds of samples quickly and accurately with ease. Moreover, the manufacturing method of the present invention enables mass production of biosensors with high preservative properties and reliability at low costs. The manufacturing method is considerably useful.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A biosensor for measuring a substrate in a liquid sample, comprising:

an insulating base plate having a principle surface, an electrode system including a working electrode and a counter electrode formed spaced apart on said principle surface of said base plate, and first and second leads respectively connected to said working electrode and said counter electrode, and a reaction layer formed on said electrode system so as to contact said working electrode and said counter electrode and including an enzyme, a hydrophilic polymer and an electron acceptor, wherein the electron acceptor is reduced by means of a reaction between the enzyme and the substrate in the liquid sample and is subsequently electrochemically oxidized and a resulting value of oxidation current between the working electrode and the counter electrode is indicative of a concentration of the substrate, and wherein said counter electrode has a substantially circular outer peripheral edge, a substantially square inner peripheral edge defining a square opening therein having four corners, and opposing generally radial edges defining a gap therebetween extending from a side of said square opening to said outer peripheral edge, wherein said working electrode has a substantially square outer periphery and is centrally located and aligned within said square opening of counter electrode, and wherein said first lead extends through said gap of said counter electrode to contact said working electrode.

2. A biosensor for measuring a substrate in a liquid sample, comprising:

an insulating base plate having a principle surface, an electrode system including a working electrode and a counter electrode formed spaced apart on said principle surface of said base plate, and first and second leads respectively connected to said working electrode and said counter electrode, and a reaction layer formed on said electrode system so as to contact said working electrode and said counter electrode and including an enzyme, a hydrophilic polymer and an electron acceptor, wherein the electron acceptor is reduced by means of a reaction between the enzyme and the substrate in the liquid sample and is subsequently electrochemically oxidized and a resulting value of oxidation current between the working electrode and the counter electrode is indicative of a concentration of the substrate, and wherein said counter electrode has a substantially circular outer peripheral edge, and an inner peripheral edge defining a rectangular opening therein having two inner corners and opposing generally radial edges extending from said two inner corners to said outer peripheral edge, wherein said working electrode has a substantially rectangular outer periphery and is centrally located and aligned within said rectangular opening of said counter electrode, and wherein an outer edge of said working electrode has an arc configuration aligned with the outer peripheral edge of said counter electrode, and wherein said first lead contacts said working electrode at said outer edge.

3. A biosensor for measuring a substrate in a liquid sample, comprising:

an insulating base plate having a principle surface, an electrode system including a working electrode and a counter electrode formed spaced apart on said principle surface of said base plate, and first and second leads respectively connected to said working electrode and said counter electrode, and a reaction layer formed on said electrode system so as to contact said working electrode and said counter electrode and including an enzyme, a hydrophilic polymer and an electron acceptor, wherein the electron acceptor is reduced by means of a reaction between the enzyme and the substrate in the liquid sample and is subsequently electrochemically oxidized and a resulting value of oxidation current between the working electrode and the counter electrode is indicative of a concentration of the substrate, and wherein said counter electrode has a substantially circular outer peripheral edge, and an inner peripheral edge defining an elongate opening therein which is devoid of inner corners and includes opposing generally radial edges defining a gap therebetween extending from a side of said elongate opening to said outer peripheral edge, wherein said working electrode has a substantially elongate outer periphery devoid of inner corners and is centrally located and aligned within said elongate opening of said counter electrode, and wherein an outer edge of said working electrode has an arc configuration aligned with the outer peripheral edge of said counter electrode, and wherein said first lead contacts said working electrode at said outer edge.

4. A biosensor as claimed in claim 3, wherein said base plate is elongate and wherein said elongate opening of said counter electrode and said working electrode extending longitudinally along said base plate.

5. A biosensor as claimed in claim 3, wherein said base plate is elongate and wherein said elongate opening of said counter electrode and said working electrode extending laterally along said base plate.

6. A biosensor for measuring a substrate in a liquid sample, comprising:

an insulating base plate having a principle surface, an electrode system including a working electrode, a counter electrode and a reference electrode formed spaced apart on said principle surface of said base plate, and first, second and third leads respectively connected to said working electrode, said counter electrode and said reference electrode at an outer edge of each electrode, and a reaction layer formed on said electrode system so as to contact said working electrode and said counter electrode and including an enzyme, a hydrophilic polymer and an electron acceptor, wherein the electron acceptor is reduced by means of a reaction between the enzyme and the substrate in the liquid sample and is subsequently electrochemically oxidized and a resulting value of oxidation current between the working electrode and the counter electrode is indicative of a concentration of the substrate, and wherein said working electrode is located between said reference electrode and said counter electrode with parallel extending gaps therebetween, and wherein said outer edges of said working electrode and said counter electrode and said reference electrode extend along a same circular configuration.

* * * * *